US00PP16036P2

(12) United States Plant Patent
Van Delft

(10) Patent No.: US PP16,036 P2
(45) Date of Patent: Oct. 11, 2005

(54) *KNIPHOFIA* PLANT NAMED 'FIRST SURPRISE'

(50) Latin Name: *Kniphofia uvaria*
Varietal Denomination: First Surprise

(75) Inventor: Luit Van Delft, Noordwykerhout (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 10/968,804

(22) Filed: Oct. 19, 2004

(51) Int. Cl.[7] ..... A01H 5/00
(52) U.S. Cl. ..... Plt./263
(58) Field of Search ..... Plt./263

*Primary Examiner*—Anne Marie Grunberg
(74) *Attorney, Agent, or Firm*—C. A. Whealy

(57) ABSTRACT

A new and distinct cultivar of *Kniphofia* plant named 'First Surprise' characterized by its relatively compact plant habit; suitability for container production; mostly upright and moderately strong flowering scapes; orange-colored flowers arranged in racemes; and early and freely flowering habit.

2 Drawing Sheets

Botanical classification/cultivar designation: *Kniphofia uvaria* cultivar First Surprise.

BACKGROUND OF THE INVENTION

The present Invention relates to a new and distinct cultivar of *Kniphofia* plant, botanically known as *Kniphofia uvaria*, and hereinafter referred to by the name 'First Surprise'.

The new *Kniphofia* is a product of a planned breeding program conducted by the Inventor in Noordwijkerhout, The Netherlands. The objective of the breeding program is to create new compact and early-flowering *Kniphofia* cultivars with attractive flower coloration.

The new *Kniphofia* originated from an open-pollination made by the Inventor in Noordwijkerhout, The Netherlands, of a proprietary seedling selection, not patented, as the female, or seed, parent with an unknown selection of *Kniphofia*, not patented, as the male, or pollen, parent. The new *Kniphofia* was discovered and selected by the Inventor as a single flowering plant within the progeny of the stated open-pollination grown in a controlled environment in Noordwijkerhout, The Netherlands in 1999. The selection of this plant was based on its relatively compact habit and good flower coloration.

Asexual reproduction of the new *Kniphofia* by divisions in a controlled environment in Noordwijkerhout, The Netherlands since 1999, has shown that the unique features of this new *Kniphofia* are stable and reproduced true to type in successive generations.

SUMMARY OF THE INVENTION

The cultivar 'First Surprise' has not been observed under all possible environmental conditions. The phenotype may vary somewhat with variations in environment such as temperature and light intensity without, however, any variance in genotype.

The following traits have been repeatedly observed and are determined to be the unique characteristics of 'First Surprise'. These characteristics in combination distinguish 'First Surprise' as a new and distinct cultivar of *Kniphofia:*

1. Relatively compact plant habit; suitable for container production.

2. Mostly upright and moderately strong flowering scapes.
3. Orange-colored flowers arranged in racemes.
4. Early and freely flowering habit.

Compared to plants of the female parent selection, plants of the new *Kniphofia* are more compact and differ in flower color.

Plants of the new *Kniphofia* can be compared to plants of the cultivar Alcazar, not patented. In side-by-side comparisons conducted in Lisse, The Netherlands, plants of the new *Kniphofia* differed from plants of the cultivar Alcazar, in the following characteristics:

1. Plants of the new *Kniphofia* were more compact than plants of the cultivar Alcazar.
2. Plants of the new *Kniphofia* flowered in May whereas plants of the cultivar Alcazar flowered in July.
3. Plants of the new *Kniphofia* and the cultivar Alcazar differed in flower color as plants of the cultivar Alcazar had orange and yellow-colored flowers.

DESCRIPTION OF THE PHOTOGRAPHS

The accompanying colored photographs illustrate the overall appearance of the new *Kniphofia*, showing the colors as true as it is reasonably possible to obtain in colored reproductions of this type. Colors in the photographs may differ slightly from the color values cited in the detailed botanical description which accurately describe the colors of the new *Kniphofia*.

The photograph on the first sheet comprises a side perspective view of a typical flowering plant of 'First Surprise' grown in an outdoor nursery.

The photograph at the top left of the second sheet is a close-up view of a typical inflorescence of 'First Surprise'.

The photograph at the bottom right of the second sheet is a close-up view of typical leaves of 'First Surprise'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe one-year old plants grown in Lisserbroek, The Netherlands under commercial practice in an outdoor nursery. During the production of the plants, day temperatures ranged from 14 to 33° C. and night temperatures ranged from 7 to 14° C. Measurements and numerical values represent averages for typical flowering plants. The photographs and the description were taken during the early summer.

Botanical classification: *Kniphofia uvaria* cultivar First Surprise.

Parentage:

*Female, or seed, parent.*—Proprietary seedling selection of *Kniphofia uvaria*, not patented.

*Male, or pollen, parent.*—Unknown selection if *Kniphofia uvaria*, not patented.

Propagation:

*Type.*—By divisions.

*Time to initiate roots.*—About 90 days at 18° C.

*Root description.*—Fine, fibrous; light brown in color. Rhizome development has not been observed.

*Rooting habit.*—Freely branching.

Plant description:

*Plant form/growth habit.*—Upright flowering plant. Leaves basal with central flowering scapes with flowers arranged on racemes. Moderately vigorous to low vigor.

*Crop time.*—Usually about five months are required to produce finished flowering plants in containers.

*Plant height, soil level to top of foliar plane.*—About 26 cm.

*Plant height, soil level to top of inflorescence.*—About 43 cm.

*Plant width.*—About 38 cm.

*Leaves.*—Arrangement: Simple; basal; rosette; sessile. Quantity of leaves per plant: About 15. Length: About 29 cm. Width: About 7 mm. Shape: Linear. Apex: Long acuminate. Base: Cuneate. Margin: Ciliate. Texture, upper and lower surfaces: Glabrous, smooth. Venation pattern: Parallel. Color: Developing leaves, upper and lower surfaces: 144A; towards the base, 144C. Fully expanded leaves, upper surface: Between 137B and 143A; towards the base, 144B to 144C. Fully expanded leaves, lower surface: 138A; towards the base, 144B. Venation, upper and lower surfaces: Similar to lamina.

Flower description:

*Flowering habit.*—Inflorescences scapose with single trumpet-shaped flowers; flowers arranged in racemes on mostly erect and moderately strong scapes. Flowers not fragrant; flowers not persistent. Flowers face outwardly to downward and drooping.

*Natural flowering season.*—Early flowering; plants flower continuously during June and July in The Netherlands.

*Flower longevity on the plant.*—About five days.

*Inflorescence size.*—Length: About 7.4 cm. Width: About 4.3 cm.

*Flower buds.*—Length: About 1.8 cm. Diameter: About 5 mm. Shape: Narrowly obovate. Color: 25A; towards the base, 25B.

*Flowers.*—Quantity of flowers per inflorescence: About 49; typically two flowering stems develop per plant. Shape: Trumpet-shaped. Diameter: About 7 mm (excluding anthers). Depth (length): About 1.6 cm (excluding anthers).

*Perianth.*—Quantity/arrangement: Six tepals per flower; 90% of tepal length is fused. Tepal length: About 1.6 cm. Tepal width: About 3 mm. Tepal shape: Narrowly oblong. Tepal apex: Acute. Tepal margin: Entire. Tepal texture, upper and lower surfaces: Smooth, glabrous. Tepal color: When opening and fully opened, upper surface: 25C; color becoming closer to 28A with development. When opening and fully opened, lower surface:25A.

*Scape.*—Angle: Mostly erect. Strength: Moderately strong. Length: About 43 cm. Diameter: About 4.5 mm. Texture: Smooth, glabrous. Color: 144A.

*Pedicels.*—Angle: About 70° C. from vertical. Strength: Strong. Length: About 2 mm. Diameter: About 1 mm. Texture: Smooth, glabrous. Color: 172B.

*Reproductive organs.*—Stamens: Quantity per flower: Six. Filament length: About 2.7 cm. Anther shape: Oblong. Anther length: About 1.7 mm. Anther color, front: 9A. Anther color, rear: 17B. Amount of pollen: Scarce. Pollen color: 8A to 8B. Pistils: Quantity per flower: One. Length: About 2.5 cm. Stigma shape: Crested. Stigma color: 16A. Style length: About 2.45 cm. Style color: 16B. Ovary color: N144C.

*Fruit/seed.*—Fruit and seed development has not been observed on plants of the new *Kniphofia*.

Disease/pest resistance: Resistance to pathogens and pests common to *Kniphofia* has not been determined.

Temperature tolerance: Plants of the new *Kniphofia* have been observed to tolerate temperatures from −20 to 40° C.

It is claimed:

1. A new and distinct cultivar of *Kniphofia* plant named 'First Surprise', as illustrated and described.

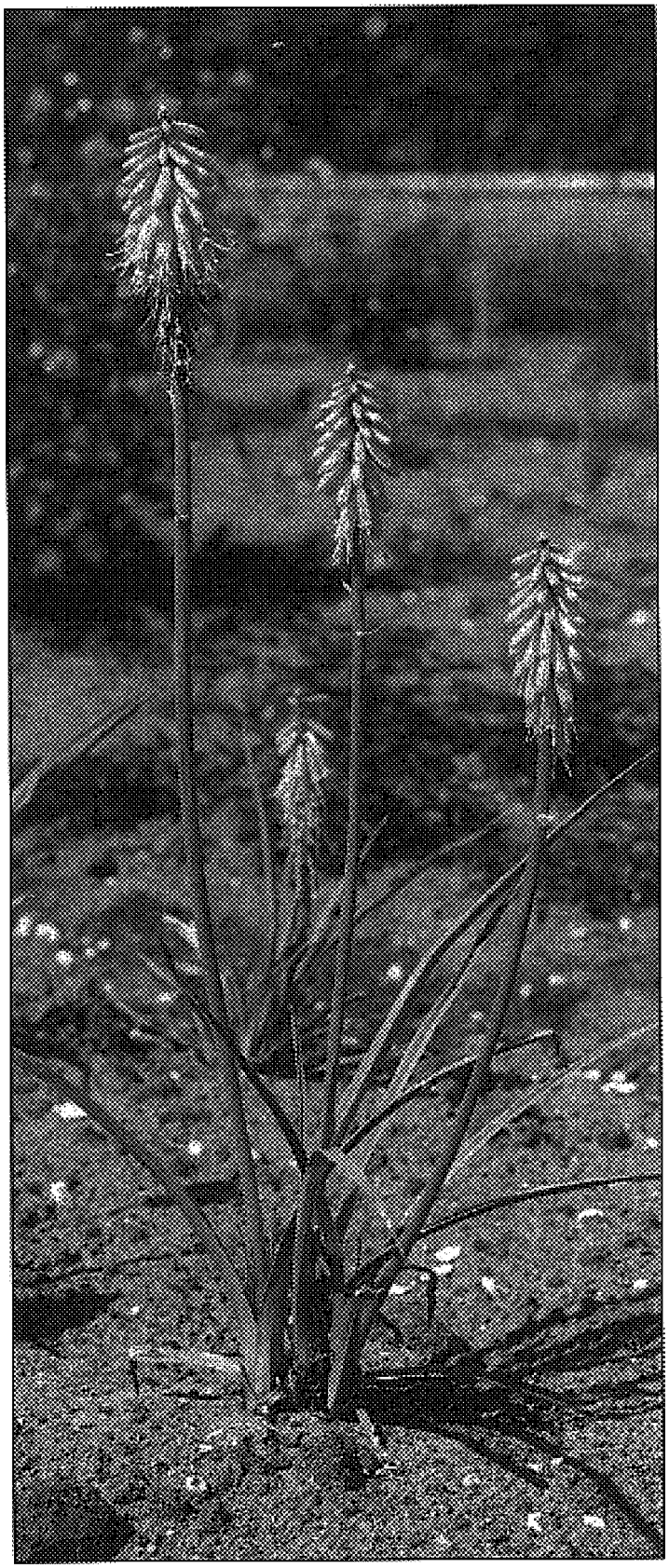

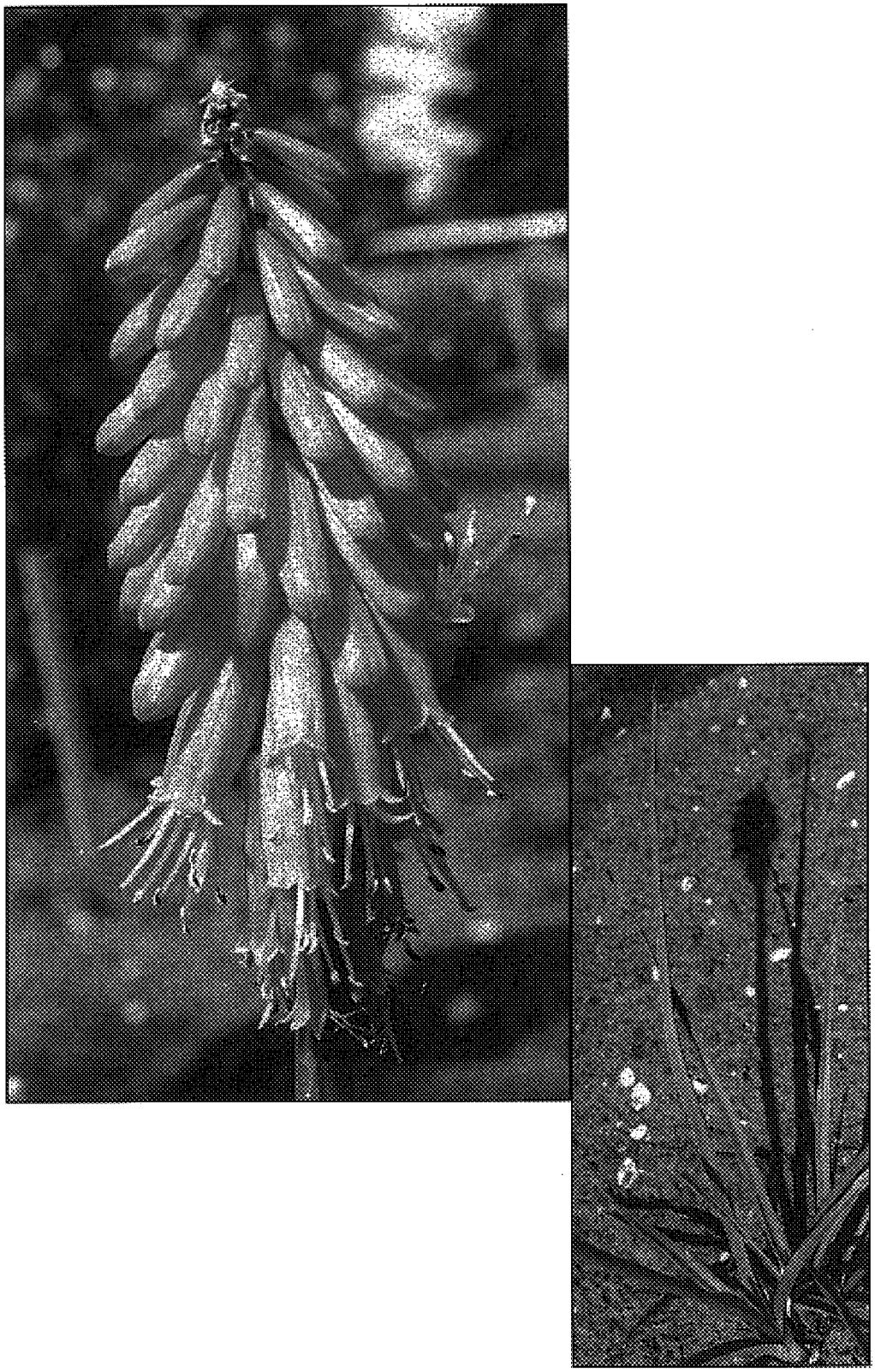

* * * * *